(12) United States Patent
Bahrami et al.

(10) Patent No.: US 10,444,827 B2
(45) Date of Patent: Oct. 15, 2019

(54) PLATFORM FOR VIRTUAL REALITY MOVEMENT

(71) Applicant: Fujitsu Limited, Kawasaki-shi, Kanagawa (JP)

(72) Inventors: Mehdi Bahrami, Santa Clara, CA (US); Wei-Peng Chen, Fremont, CA (US); Takuki Kamiya, San Jose, CA (US)

(73) Assignee: Fujitsu Limited, Kawasaki (JP)

( * ) Notice: Subject to any disclaimer, the term of this patent is extended or adjusted under 35 U.S.C. 154(b) by 123 days.

(21) Appl. No.: 15/707,502

(22) Filed: Sep. 18, 2017

(65) Prior Publication Data
US 2019/0086996 A1  Mar. 21, 2019

(51) Int. Cl.
*A63B 19/04* (2006.01)
*A63B 22/02* (2006.01)
(Continued)

(52) U.S. Cl.
CPC .............. *G06F 3/011* (2013.01); *A63G 31/16* (2013.01); *G02B 27/0093* (2013.01);
(Continued)

(58) Field of Classification Search
CPC . A63B 19/04; A63B 21/0125; A63B 22/0017; A63B 22/0605; A63B 22/0257; A63B 22/02; A63B 22/0235; A63B 22/0242; A63B 22/025; A63B 22/06; A63B 22/14; A63B 22/0285; A63B 24/00;
(Continued)

(56) References Cited

U.S. PATENT DOCUMENTS 5,562,572 A * 10/1996 Carmein .................. A61H 3/00
                                                                  482/4
5,690,587 A * 11/1997 Gruenangerl .......... A63B 22/02
                                                                  482/54
(Continued)

OTHER PUBLICATIONS

Team, Brain and Spine. "Virtual Reality Treadmill a High-Tech Help for Patients (Video)." Health Essentials from Cleveland Clinic. Retrieved from <https://health.clevelandclinic.org/2014/05/virtual-reality-treadmill-helps-patients-with-parkinsons-ms/>, Jul. 17, 2015; 10 pages.

(Continued)

*Primary Examiner* — Michael J Eurice
(74) *Attorney, Agent, or Firm* — Baker Botts L.L.P.

(57) ABSTRACT

In one or more embodiments, one or more systems, methods, and/or processes may provide first images to a user; determine a rotation of a head of the user; provide second images, based at least on the rotation, to the user; and rotate a platform in accordance with the rotation. In one example, the platform may include a movement belt, and one or more of a walking movement and a running movement of the user may be determine via the movement belt. In another example, one or more optical sensors may be utilized to determine movements of the user. In one or more embodiments, determining the rotation of the head of the user may include utilizing one or more of a gyroscope and an accelerometer of a head mounted display, worn by the user. For example, the head mounted display may provide images of a virtual reality environment to the user.

20 Claims, 12 Drawing Sheets

(51) Int. Cl.
    *A63B 22/06*         (2006.01)
    *A63B 22/14*         (2006.01)
    *G06F 3/01*           (2006.01)
    *A63G 31/16*         (2006.01)
    *G02B 27/00*         (2006.01)
    *G02B 27/01*         (2006.01)
    *G09B 9/00*           (2006.01)
    *A63B 24/00*         (2006.01)

(52) U.S. Cl.
    CPC ........ *A61M 2205/507* (2013.01); *A63B 19/04* (2013.01); *A63B 22/02* (2013.01); *A63B 22/06* (2013.01); *A63B 22/14* (2013.01); *A63B 24/00* (2013.01); *G02B 27/017* (2013.01); *G02B 2027/0187* (2013.01); *G06F 3/012* (2013.01); *G06F 2203/012* (2013.01); *G09B 9/00* (2013.01)

(58) Field of Classification Search
    CPC ............ A63B 24/0062; A63B 71/0619; A63B 71/0622; A63B 2022/0271; A63B 2024/0096; A63B 2071/0638; A63B 2071/0666; A63B 2071/0636; A63B 2071/0644; A63B 2022/0278; A63B 2220/80; A63B 2220/34; A63B 2220/833; A63B 2225/50; G06F 3/012; G06F 2203/012; A61M 2205/507
    See application file for complete search history.

(56) References Cited

U.S. PATENT DOCUMENTS

| | | | | |
|---|---|---|---|---|
| 5,846,134 | A * | 12/1998 | Latypov | A63B 19/04 463/46 |
| 5,948,990 | A | 9/1999 | Hashida | |
| 5,961,541 | A | 10/1999 | Ferrati | |
| 5,980,256 | A * | 11/1999 | Carmein | A63B 22/02 434/29 |
| 6,050,822 | A * | 4/2000 | Faughn | G06F 3/011 345/952 |
| 6,102,832 | A * | 8/2000 | Tani | G06F 3/011 482/4 |
| 6,123,647 | A * | 9/2000 | Mitchell | A63B 22/02 198/456 |
| 6,135,928 | A * | 10/2000 | Butterfield | G06F 3/011 482/66 |
| 6,152,854 | A * | 11/2000 | Carmein | A63B 22/025 482/4 |
| 6,743,154 | B2 * | 6/2004 | Epstein | A63B 22/02 482/51 |
| 7,037,241 | B2 | 5/2006 | Kuo | |
| 7,381,152 | B2 | 6/2008 | Couvillion et al. | |
| 7,387,592 | B2 | 6/2008 | Couvillion et al. | |
| 7,399,258 | B1 * | 7/2008 | Sugar | A63B 22/0235 482/51 |
| 7,470,218 | B2 | 12/2008 | Williams | |
| 7,682,291 | B2 | 3/2010 | Gill et al. | |
| 7,780,573 | B1 * | 8/2010 | Carmein | A63B 22/0242 482/4 |
| 7,811,200 | B2 | 10/2010 | Chiang | |
| 7,841,964 | B2 | 11/2010 | Radow | |
| 8,083,647 | B2 | 12/2011 | Park | |
| 8,414,130 | B2 | 4/2013 | Pelah | |
| 8,790,279 | B2 | 7/2014 | Brunner | |
| 2001/0043232 | A1 * | 11/2001 | Abbott | G06F 1/163 715/700 |
| 2002/0103616 | A1 * | 8/2002 | Park | G06F 1/3203 702/150 |
| 2002/0105482 | A1 * | 8/2002 | Lemelson | G06F 3/013 345/7 |
| 2003/0103016 | A1 * | 6/2003 | Walker | G02B 27/017 345/7 |
| 2004/0048722 | A1 * | 3/2004 | Epstein | A63B 22/02 482/54 |
| 2004/0063549 | A1 * | 4/2004 | Kuo | A63B 22/0242 482/54 |
| 2004/0242390 | A1 * | 12/2004 | Willliams | A63B 23/0464 482/146 |
| 2005/0108096 | A1 * | 5/2005 | Burger | G06F 21/32 705/14.38 |
| 2005/0148432 | A1 * | 7/2005 | Carmein | A63B 22/0235 482/8 |
| 2005/0266963 | A1 * | 12/2005 | Holmes | A63B 22/02 482/54 |
| 2006/0114171 | A1 | 6/2006 | Vascotto et al. | |
| 2006/0139317 | A1 * | 6/2006 | Leu | G06F 3/011 345/156 |
| 2007/0229397 | A1 | 10/2007 | Sefton | |
| 2007/0233615 | A1 * | 10/2007 | Tumminaro | G06Q 20/12 705/75 |
| 2007/0270285 | A1 * | 11/2007 | Gill | A63B 22/02 482/54 |
| 2008/0019569 | A1 * | 1/2008 | Rhoads | G06F 3/017 382/107 |
| 2008/0033641 | A1 * | 2/2008 | Medalia | G06F 3/04815 701/533 |
| 2009/0058850 | A1 * | 3/2009 | Fun | A63F 13/06 345/419 |
| 2009/0111670 | A1 * | 4/2009 | Williams | A63B 23/0464 482/146 |
| 2009/0124938 | A1 * | 5/2009 | Brunner | A61B 5/1038 600/595 |
| 2009/0152343 | A1 * | 6/2009 | Carter | G06Q 10/0633 235/379 |
| 2009/0160609 | A1 * | 6/2009 | Lin | G06F 21/32 340/5.83 |
| 2009/0175509 | A1 * | 7/2009 | Gonion | G06F 1/3231 382/118 |
| 2009/0262087 | A1 * | 10/2009 | Kim | G06F 3/0488 345/173 |
| 2010/0022358 | A1 * | 1/2010 | Schwaiger | A63B 22/0242 482/54 |
| 2010/0048256 | A1 * | 2/2010 | Huppi | H04M 1/72563 455/574 |
| 2010/0075808 | A1 * | 3/2010 | Luberski | A63B 22/18 482/8 |
| 2010/0113222 | A1 * | 5/2010 | Radow | A63B 22/0235 482/5 |
| 2010/0147430 | A1 * | 6/2010 | Shultz | B60O 7/18 152/450 |
| 2010/0265171 | A1 * | 10/2010 | Pelah | A63F 13/00 345/157 |
| 2010/0300006 | A1 | 12/2010 | Magpuri | |
| 2011/0009241 | A1 * | 1/2011 | Lane | A63B 24/0087 482/8 |
| 2011/0035594 | A1 * | 2/2011 | Fox | G06Q 30/02 713/170 |
| 2011/0177914 | A1 * | 7/2011 | Park | A63B 24/0062 482/1 |
| 2011/0209192 | A1 * | 8/2011 | LeClerc Greer | G06F 21/32 726/1 |
| 2011/0263355 | A1 * | 10/2011 | Delorme | A63B 69/0026 473/446 |
| 2011/0276396 | A1 * | 11/2011 | Rathod | G06Q 10/00 705/14.49 |
| 2012/0142442 | A1 * | 6/2012 | Brantingham | A63B 69/0079 473/140 |
| 2012/0144461 | A1 * | 6/2012 | Rathbun | H04L 9/3213 726/5 |
| 2012/0190504 | A1 * | 7/2012 | Lee | G06F 19/3481 482/8 |
| 2012/0302408 | A1 * | 11/2012 | Burger | A63B 21/0087 482/54 |
| 2013/0073400 | A1 * | 3/2013 | Heath | G06Q 30/02 705/14.73 |
| 2013/0127980 | A1 * | 5/2013 | Haddick | G06F 3/013 348/14.08 |

(56) References Cited

U.S. PATENT DOCUMENTS

| | | | |
|---|---|---|---|
| 2013/0132854 A1* | 5/2013 | Raleigh | G06F 3/0482 715/738 |
| 2013/0132910 A1* | 5/2013 | Belmon | G06F 3/011 715/850 |
| 2013/0167226 A1* | 6/2013 | Lin | H04M 1/0256 726/19 |
| 2013/0278631 A1* | 10/2013 | Border | G02B 27/017 345/633 |
| 2013/0311572 A1* | 11/2013 | Faller | H04L 65/403 709/204 |
| 2014/0059443 A1* | 2/2014 | Tabe | H04L 51/32 715/738 |
| 2014/0062855 A1* | 3/2014 | Huang | G09G 5/00 345/156 |
| 2014/0162598 A1* | 6/2014 | Villa-Real | H04M 1/66 455/411 |
| 2015/0070274 A1* | 3/2015 | Morozov | G06F 3/0346 345/156 |
| 2015/0321337 A1* | 11/2015 | Stephens, Jr. | B25J 9/1689 700/257 |
| 2016/0199695 A1* | 7/2016 | Armstrong | A63B 22/0235 482/8 |
| 2017/0036111 A1* | 2/2017 | Shigeta | G01C 21/165 |
| 2017/0043252 A1* | 2/2017 | Kalaboukis | A63F 13/02 |
| 2017/0129105 A1* | 5/2017 | Stephens, Jr. | B25J 11/00 |
| 2017/0168486 A1 | 9/2017 | Tommy et al. | |
| 2017/0272838 A1* | 9/2017 | Glazer | H04N 21/8146 |
| 2017/0336860 A1* | 11/2017 | Smoot | G06F 3/011 |
| 2018/0033321 A1* | 2/2018 | Clarke | B29D 23/00 |
| 2018/0036880 A1* | 2/2018 | Stephens, Jr. | A63B 22/0023 |
| 2018/0050256 A1* | 2/2018 | Buvid | A63B 71/0622 |
| 2018/0147442 A1* | 5/2018 | Moon | A63B 22/025 |
| 2018/0161620 A1* | 6/2018 | Rothschild | A63B 71/06 |
| 2018/0170678 A1* | 6/2018 | Leong | A63B 22/0285 |
| 2018/0217586 A1* | 8/2018 | Stephens, Jr. | A61B 5/7264 |
| 2018/0224928 A1* | 8/2018 | Ross | G06F 3/011 |
| 2018/0326286 A1* | 11/2018 | Rathi | A63B 71/0622 |
| 2018/0360340 A1* | 12/2018 | Rehse | A63B 24/0062 |

OTHER PUBLICATIONS

"Virtuix Omni Package." Virtuix Omni. Retrieved from < http://www.virtuix.com/product/omni-package/#tabs_20141211-190917-6490>, Jul. 18, 2017; 3 pages.

Philip Wong, "Virtual Reality Treadmill: Run with a View." CNET, Retrieved from < https://www.cnet.com/news/virtual-reality-treadmill-run-with-a-view/#>, Jul. 30, 2008; 1 page.

"Kat Walk—A New VR Omni-Directional Treadmill." Kickstarter, Retrieved from < https://www.kickstarter.com/projects/katvr/kat-walk-a-new-virtual-reality-locomotion-device>, Jul. 18, 2017; 24 pages.

"The World's First True Commercially Viable Omnidirectional Treadmill." Infinadeck Omnidirectional Treadmill. Retrieved from < http://www.infinadeck.com/#introduction >, Jul. 18, 2017; 6 pages.

"Virtual Reality Setups." Cyberith, Retrieved from < http://cyberith.com/product/>, Jul. 18, 2017; 4 pages.

"Virtual Reality's Locomotion Problem." Motherboard, Retrieved from < http://motherboard.vice.com/read/virtual-realitys-locomotion-problem>, Jul. 18, 2017; 14 pages.

Sheik-Nainar, Mohamed A., and David B. Kaber. "The utility of a virtual reality locomotion interface for studying gait behavior." Human factors 49.4, (2007): 696-709; 14 pages.

"Omnidirectional Treadmill." Wikipedia. Wikimedia Foundation, Jul. 12, 2017. Retrieved from < https://en.wikipedia.org/wiki/Omnidirectional_treadmill >; 2 pages.

"Cave Automatic Virtual Environment." Wikipedia. Wikimedia Foundation, Jul. 16, 2017. Retrieved from < https://en.wikipedia.org/wiki/Cave_automatic_virtual_environment>; 6 pages.

John Marco, "List of Omnidirectional Treadmills Under Development." Virtual Reality Times. Dec. 6, 2016. Retrieved from < http://www.virtualrealitytimes.com/2015/04/09/list-of-omnidirectional- treadmills-under-development/>; 11 pages.

* cited by examiner

PLATFORM FOR VIRTUAL REALITY MOVEMENT

BACKGROUND

Field of the Disclosure

The present disclosure relates to a platform for virtual reality movement.

Description of the Related Art

In the past, virtual reality (VR) systems lacked abilities that would allow natural human movement, such as walking, jogging, running, etc, and navigation of a VR environment was typically experienced via pointing, gesturing, manipulating a joystick, a trackball, or a mouse. Moreover, some VR environments simulate human movement while a user sits or stands. Furthermore, there is a growing demand for exercise machines to be entertaining by enhancing a physical exertion experience through three-dimensional visual graphics. Further, utilizing multi-directional virtually unrestricted movement within a VR environment and within a physically restricted space has also been desirable.

SUMMARY

In one or more embodiments, one or more systems may include a first platform that has a top surface, which is substantially planar and configured to rotate and support a user, and the one or more systems may provide first images to a user; determine a rotation of a head of the user; provide second images, based at least on the rotation, to the user; and rotate the first platform in accordance with the rotation.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION

Figure 1A:
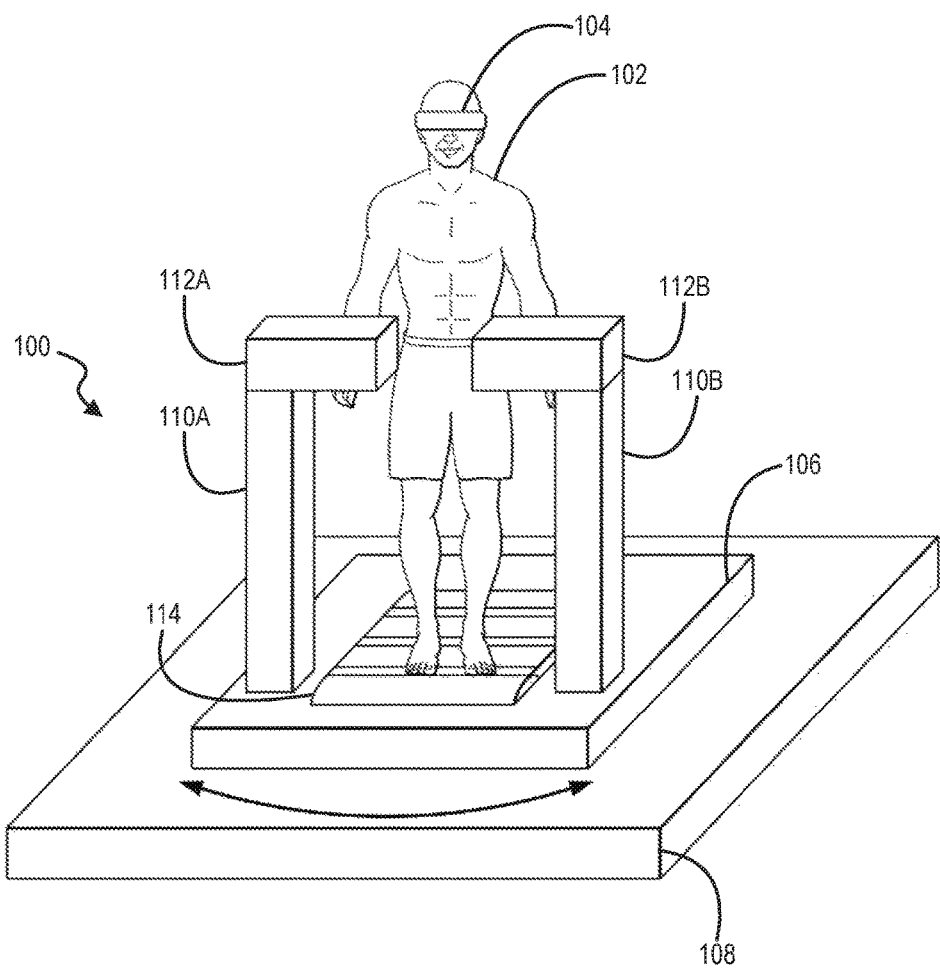
FIGS. 1A-1C illustrate a virtual reality movement system, according to one or more embodiments.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a reference numeral followed by a letter refers to a specific instance of an element and the numeral only form of the reference numeral refers to the collective element. Thus, for example, device '12A' refers to an instance of a device class, which may be referred to collectively as devices '12' and any one of which may be referred to generically as a device '12'.

In one or more embodiments, a virtual reality (VR) environment may be or include a computer-generated illusion that allows and/or permits a user (e.g., a person) to experience and/or interact with an artificially created world and/or a simulation of an environment. For example, a VR environment may stimulate naturally occurring senses such as one or more of sight, sound, touch, and movement. In one or more embodiments, the user may perform one or more actions, which may be translated by a computer system into one or more actions that affect the VR environment. In one or more embodiments, one or more systems, methods, and/or processes described herein may allow and/or permit the user to wear a VR head mounted display (HMD) that may allow and/or permit the person to move around in a VR environment. For example, the person may walk or run in the VR environment.

In one or more embodiments, one or more systems, methods, and/or processes described herein may include a virtual reality movement system (VRMS) that may include multiple planes. For example, the VRMS may include a first platform that may include a first plane and may include a second platform that may include a second plane that may rotate on the first plane. For instance, when the user moves the VR HMD left or right, the second plane may rotate on the first plane left or right, respectively to rotational movement of the VR HMD. In one or more embodiments, the VRMS may provide virtual infinite movement (e.g., walking, jogging, running, etc.) on the first platform. For example, the VRMS may include a movement belt, which may permit the user to walk, jog, run, etc. For instance, the movement belt may be similar to a treadmill. In one or more embodiments, forward and/or backward movement may be determined utilizing the movement belt. For example, sensors within and/or coupled to the movement belt may determine if the user is moving. In one instance, the sensors within and/or coupled to the movement belt may determine if the user is moving forward. In another instance, the sensors within and/or coupled to the movement belt may determine if the user is moving backward.

In one or more embodiments, the first platform may include the movement belt, and the movement belt may be rotated when there is rotational movement to a left or a right direction for the VR HMD. For example, the VR HMD may include one or more sensors that may sense and/or determine rotational movement. In one or more embodiments, the movement belt may move (e.g., forward or backward) once the user moves. In one example, the VRMS may include one or more sensors that may determine movement of one or more feet of the user. In another example, the VRMS may include one or more sensors that may determine movement of one or two legs of the user. In one or more embodiments, the VRMS may include one or more pillars and/or rails that may aid the user in maintaining balance before and/or after a movement is commenced. In one example, a rail may be parallel to the first platform. In another example, a pillar may be perpendicular to the first platform. In one or more embodiments, one or more pillars and/or rails may include one or more controller devices. For example, the one or more controller devices may permit the user to control the VR HMD and/or the VRMS. For instance, the user may actuate the one or more controller devices. In one or more embodiments, the VRMS may include an embedded game pad. For example, the embedded game pad may receive input from the user. For instance, the user may "click on" one or more options via the game pad to control the VR HMD, the VRMS, the VR environment, a game, and/or a simulation, among others.

In one or more embodiments, the VRMS and the VR HMD may allow and/or permit the user to experience a three-dimensional VR environment. For example, the user may walk through a virtual area (e.g., a virtual walking tour). In one instance, when a virtual reality of a path is available for a participant, the user may be able to walk in a recorded path. In another instance, a tourist (e.g., the user) may utilize the VRMS to explore one or more three hundred and sixty (360) degree views of an area (e.g., an area of a city, an area of a country, etc.) utilizing pre-recorded VR paths and/or routes, among others.

Turning now to FIGS. 1A-1H, a virtual reality movement system is illustrated, according to one or more embodiments. FIGS. 1A-1H are schematic illustrations and are not drawn to scale. A shown in FIG. 1A, a VRMS 100 may provide a platform for virtual reality movement of a user 102. As illustrated, user 102 may wear a VR HMD 104. In one or more embodiments, VR HMD 104 may provide images and/or videos to user 102. For example, VR HMD 104 may provide images and/or videos of one or more areas and/or one or more chambers to user 102. In one or more embodiments, VR HMD 104 may provide VR images and/or VR videos to user 102. For example, VR HMD 104 may be utilized in one or more applications, such as simulators, trainers, etc. For instance, the VR images may include three-dimensional images, and/or the VR videos may include three-dimensional videos. In one or more embodiments, VR HMD 104 may include one or more monaural sound producing devices, one or more stereo sound producing devices, one or more microphones, one or more image producing devices, one or more eye tracking sensors, and/or one or more motion tracking sensors, among others. In one example, VR HMD 104 may be a stereoscopic HMD, which may provide separate images and/or separate videos for each eye of user 102. In another example, the one or more motion tracking sensors may include one or more gyroscopes and/or one or more accelerometers, among others.

As shown, VRMS 100 may include a platform 106 that may rotate upon a platform 108. In one or more embodiments, platform 106 may rotate upon platform 108 when user 102 rotates his or her head. For example, platform 106 may rotate upon platform 108 as indicated via the dashed arc, while platform 108 may stay fixed. In one instance, when user 102 rotates his or her head left, platform 106 may rotate left upon platform 108. In another instance, when user 102 rotates his or her head right, platform 106 may rotate right upon platform 108. In one or more embodiments, VR HMD 104 may include one or more sensors that may be utilized in determining a rotation of the head of user 102. In one example, the one or more sensors may include one or more gyroscopes. In another example, the one or more sensors may include one or more accelerometers.

As illustrated, VRMS 100 may include pillars 110 and rails 112. In one or more embodiments, pillars 110 and rails 112 may aid user 102 in maintaining balance. For example, user 102 may handle one or more of rails 112 in maintaining balance. In one or more embodiments, one or more of rails 112 may include one or more controller devices. In one example, the one or more controller devices may permit user 102 to control one or more of VR HMD 104 and VRMS 100, among others. In one instance, the one or more controller devices may permit user 102 to control one or more rotations of platform 106 upon platform 108. In another instance, the one or more controller devices may include an emergency brake that may be actuated by user 102. In another example, the one or more controller devices may include a game pad. For instance, the game pad may permit user 102 to control one or more of VR HMD 104 and VRMS 100, among others.

Figure 1B:
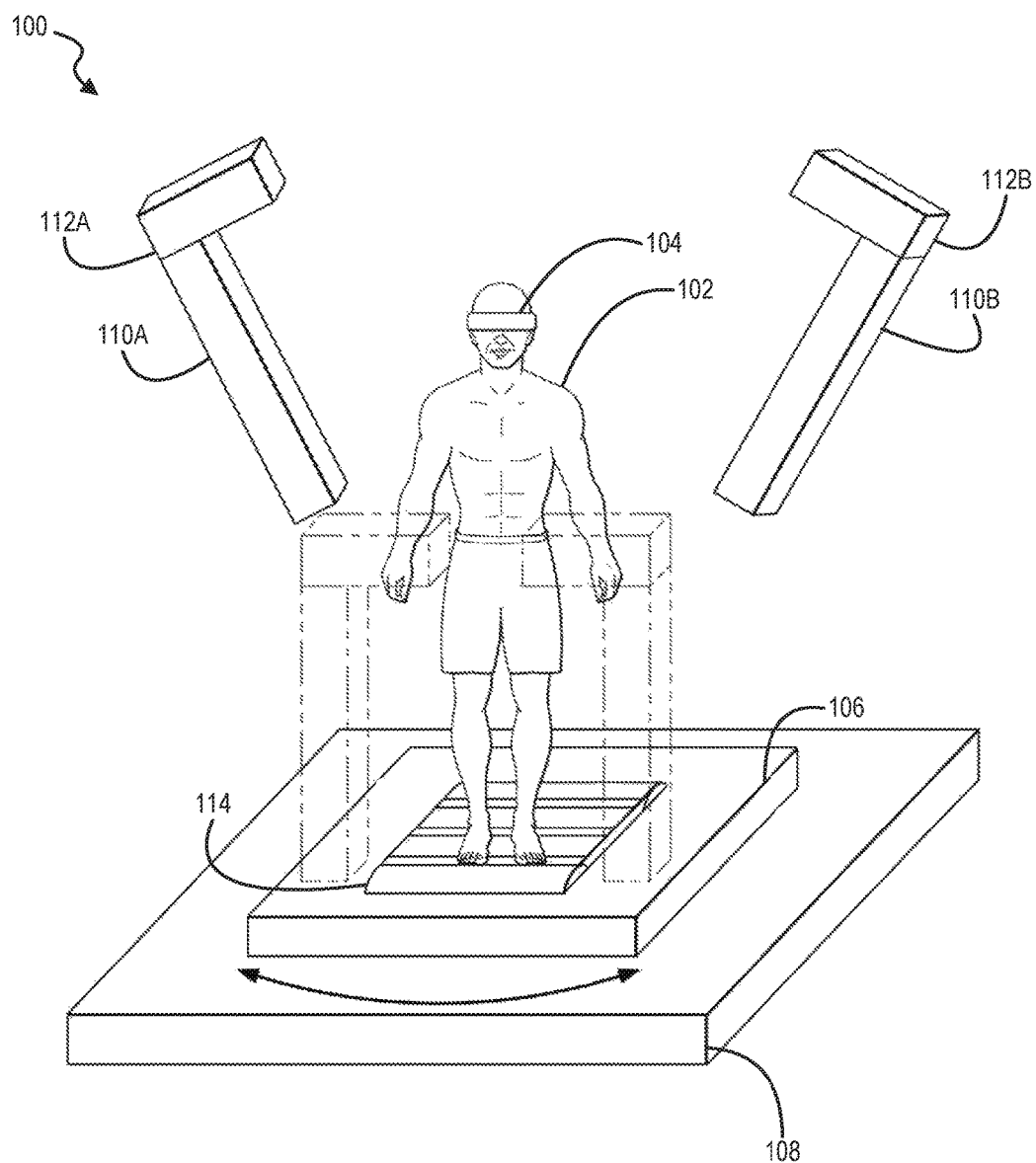

In one or more embodiments, pillars 110 and/or rails 112 may be removable and/or optional. For example, FIG. 1B illustrates removing pillars 110 and/or rails 112. For instance, pillars 110 may be coupled to platform 106 via one or more of a friction fit, mortise and tenon joinery, bolts, quick pins, magnetic contact, clamps, and through tenons, among others.

As shown, VRMS 100 may include a movement belt 114. In one or more embodiments, movement belt 114 may permit user 102 to walk and/or run. For example, movement belt 114 may be similar to a treadmill. In one instance, movement belt 114 may include a top layer that may include rubber, natural rubber, fabric reinforced rubber, etc. In a second instance, a surface of platform 106 may be planar or substantially planar, and movement belt 114 may be planar or substantially planar and may be included in platform 106 via the top surface of platform 106. In a third instance, travel in a VR of user 102 may not be limited via utilization of movement belt 114. In another instance, movement belt 114 may permit a simulated infinite travel of user 102. In one or more embodiments, forward and/or backward movement may be determined utilizing movement belt 114. For example, sensors within and/or coupled to movement belt 114 may determine if user 102 is moving. In one instance, the sensors within and/or coupled to movement belt 102 may determine if user 102 is moving forward. In a second instance, the sensors within and/or coupled to the movement belt may determine if user 102 is moving backward. In another instance, movement belt 114 may include one or more pressure sensors and/or one or more torque sensors that may sense and/or determine if user 102 is moving and/or information associated with movements of user 102 (e.g., a speed of movement, a direction of movement, an acceleration of movement, etc.). In one or more embodiments, movement belt 114 may move (e.g., forward or backward) once user 102 moves.

Figure 1C:
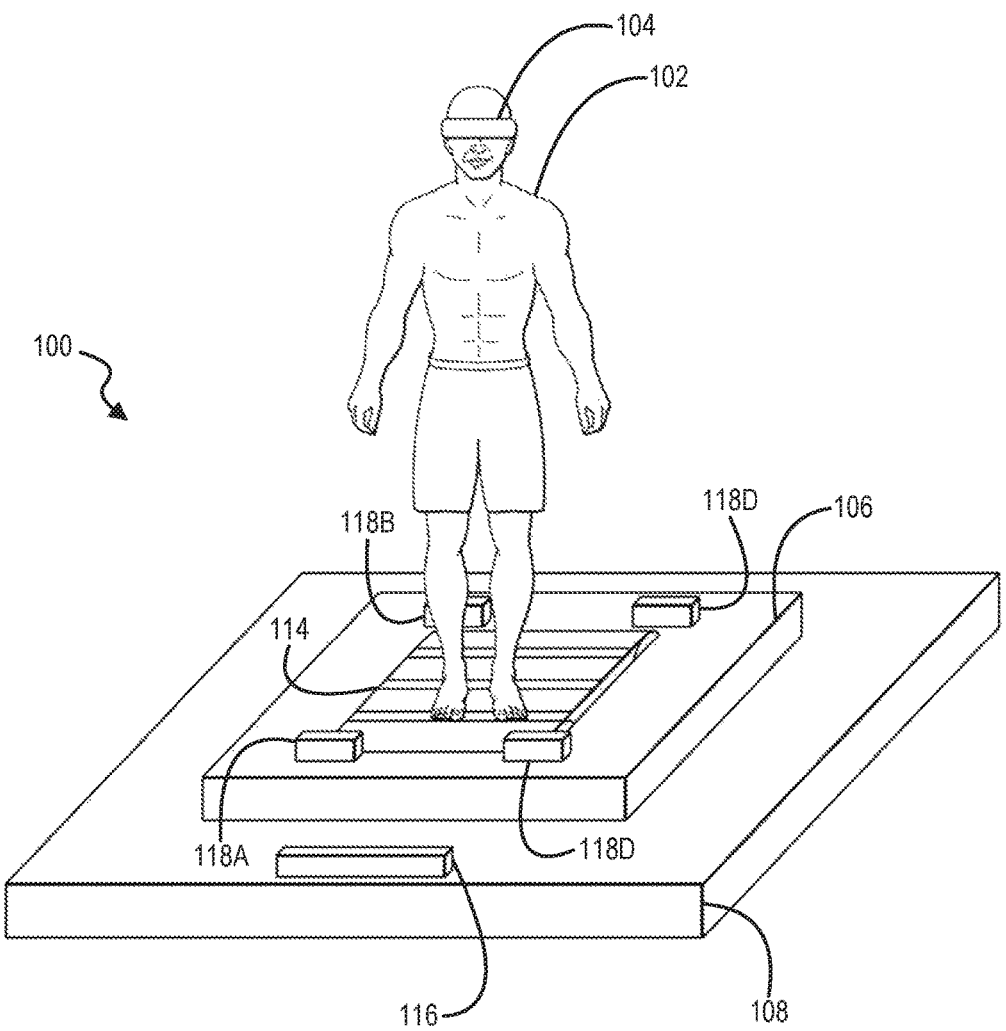

As illustrated in FIG. 1C, VRMS 100 may include a sensor 116 that may determine movement of one or two feet of user 102, in one example. For instance, sensor 116 may include one or more motion sensors, which may determine one or more motions of one or two feet of user 102. In a second example, sensor 116 may sense and/or determine one or more gestures of user 102 (e.g., one or more gestures from one or more hands and/or arms of user 102). In a third example, VRMS 100 may include sensors 118 that may determine movement of one or two legs of user 102. For instance, sensor 118 may include one or more motion sensors, which may determine one or more motions of one or two legs of user 102. In another example, sensors 118 may sense and/or determine one or more gestures of user 102 (e.g., one or more gestures from one or more hands and/or arms of user 102). In one or more embodiments, one or more of sensors 116 and 118 may include one or more projectors, one or more image sensors, one or more cameras, and/or one or more depth sensors, among others. For example, one or more of sensors 116 and 118 may receive light from objects that may be illuminated via the one or more projectors and may determine one or more positions and/or movements of a leg and/or a foot of user 102. For instance, one or more of sensors 116 and 118 may be or include a KINECT device from MICROSOFT Corporation. In one or more embodiments, one or more of sensors 116 and 118 may record one or more images and/or one or more videos via the one or more image sensors and/or the one or more cameras.

In one or more embodiments, one or more of sensors 116 and 118 may include one or more sound producing devices and/or one or more sound receiving devices. For example, the one or more sound receiving devices may receive sounds produced by the one or more sound producing devices, and one or more distances, positions, and/or motions of a leg and/or a foot of user 102 may be determined from sound interruption and/or sound reflection. For instance, one or more of sensors 116 and 118 may include one or more sonar devices. In one or more embodiments, one or more of sensors 116 and 118 may be utilized in determining one or more gestures of user 102. In one example, user 102 may utilize one or more gestures to control VRMS 100. In another example, user 102 may utilize one or more gestures to control and/or interact with a VR environment.

Figure 1D:
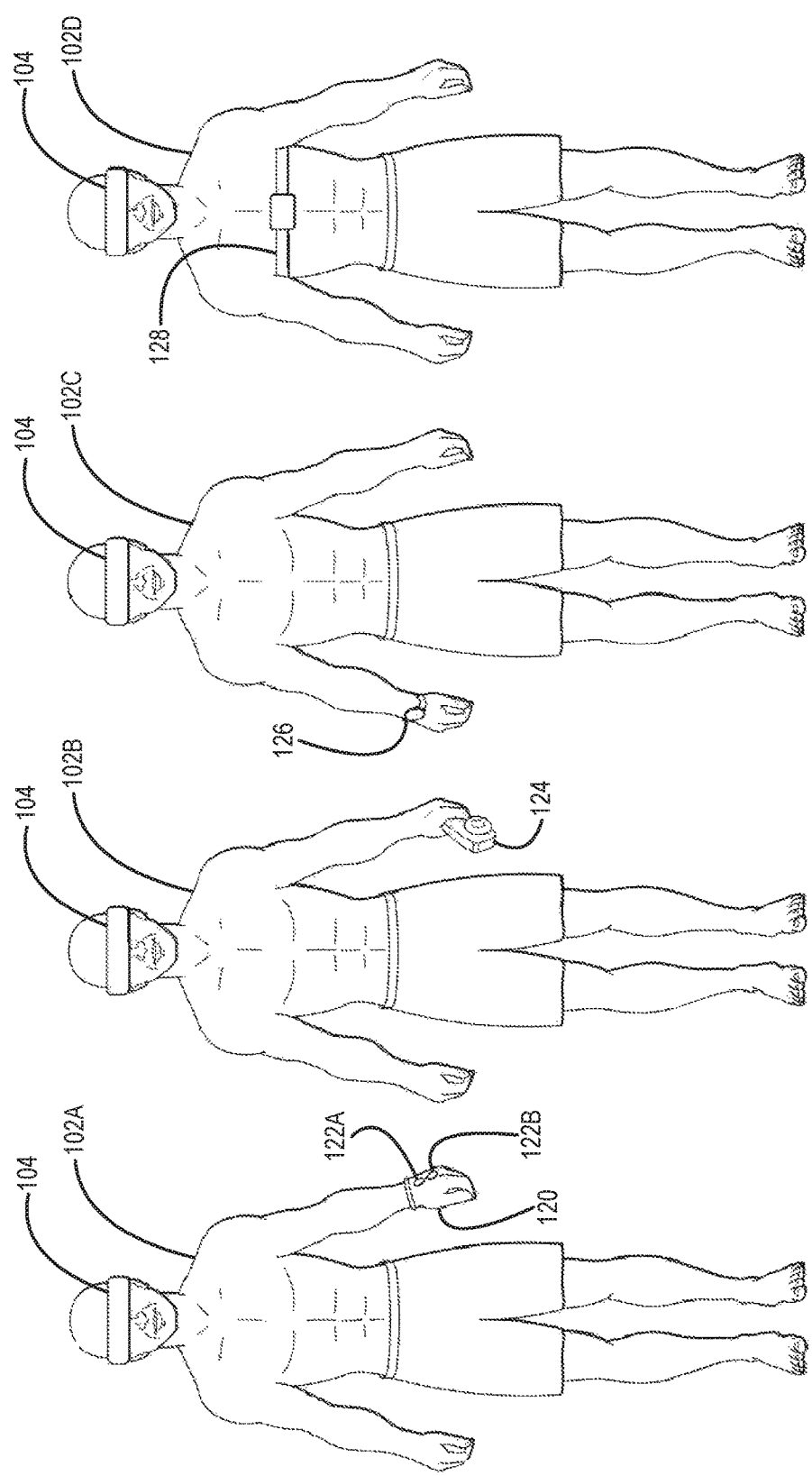
FIG. 1D illustrates various user devices, according to one or more embodiments.

As illustrated in FIG. 1D, user 102A may wear a glove 120 that may include one or more sensors and/or buttons 122A and 122B. In one example, one or more of buttons 122A and 122B may be actuated to stop movement belt 114. For instance, one or more buttons 122A and 122B may be actuated to engage and/or actuate a brake and/or a braking system that may stop movement belt 114. In another example, one or more of buttons 122A and 122B may be actuated to start and/or stop a VR simulation, a VR game, and/or a VR tour, among others. As shown, user 102B may hold and/or utilize a controller 124. In one example, controller 124 may be utilized to stop movement belt 114. In another example, controller 124 may be utilized to start and/or stop a VR simulation and/or a VR tour.

As illustrated, user 102C may wear a device 126. In one or more embodiments, device 126 may monitor and/or measure one or more biometrics of user 102. For example, device 126 may monitor and/or measure one or more of a heart rate, a blood pressure, and an oxygen saturation. For instance, device 126 may include one or more of a light-emitting diode (LED) and a photodiode, among others, which may be utilized in monitoring and/or measuring one or more biometrics of user 102. In one or more embodiments, device 126 may include a form of a watch and/or a bracelet. As illustrated, user 102D may wear a chest belt 128. In one or more embodiments, device 128 may monitor and/or measure one or more biometrics of user 102D. For example, device 128 may monitor and/or measure one or more of a heart rate, a blood pressure, and an oxygen saturation of user 102D. For instance, device 126 may one or more of a LED and a photodiode, among others, which may be utilized in monitoring and/or measuring one or more biometrics of user 102D.

In one or more embodiments, one or more of glove 120, controller 124, device 126, and chest belt 128 may communicate with VRMS 100 in a wireless fashion. For example, one or more of glove 120, controller 124, device 126, and chest belt 128 may receive data from VRMS ins a wireless fashion and/or may provide data to VRMS 100 in a wireless fashion.

Figure 1E:
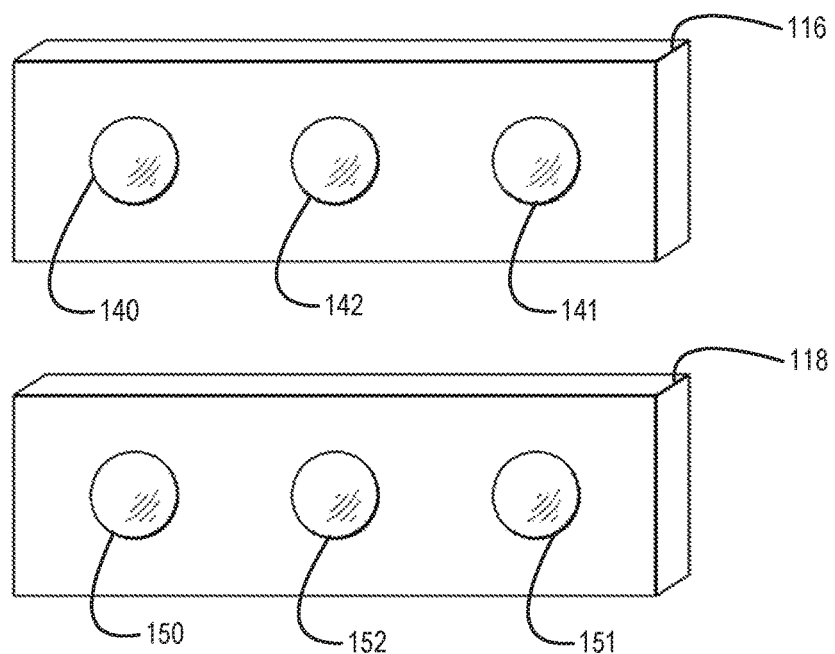
FIGS. 1E and 1F illustrate further details of sensors of the virtual reality movement system.

As illustrated in FIG. 1E, sensor 116 may include depth sensors 140 and 141 and a camera 142. In one or more embodiments, one or more of depth sensors 140 and 141 may include one more of a projector (e.g., an infrared projector) and an optical sensor, among others. In one or more embodiments, two or more of depth sensors 140 and 141 and camera 142 may be combined. As shown, sensor 118 may include depth sensors 150 and 151 and a camera 152. In one or more embodiments, one or more of depth sensors 150 and 151 may include one more of a projector (e.g., an infrared projector) and an optical sensor, among others. In one or more embodiments, two or more of depth sensors 150 and 151 and camera 152 may be combined.

Figure 1F:
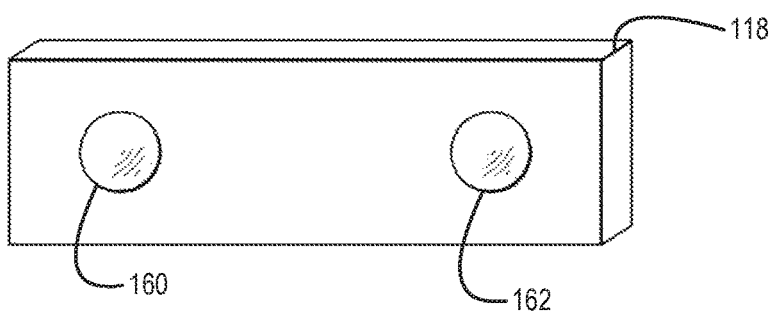

As illustrated in FIG. 1F, sensor 118 may include a sound producing device 160 and a sound receiving device 162. In one example, sound producing device 160 may include a speaker. In another example, sound receiving device 162 may include microphone. In one or more embodiments, sound producing device 160 and sound receiving device 162 may include, form, and/or implement a sonar device. In one or more embodiments, sound producing device 160 and sound receiving device 162 may be combined. For example, sound producing device 160 and sound receiving device 162 may include, form, and/or implement a transducer.

Figure 1G:
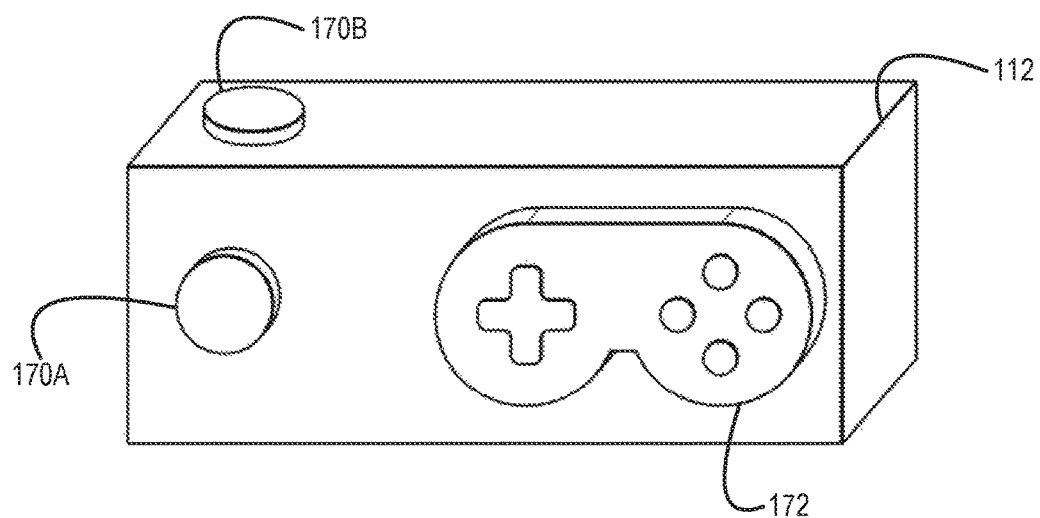
FIG. 1G illustrates a handrail that includes a gamepad and buttons, according to one or more embodiments.

As illustrated in FIG. 1G, hand rail 112 may include one or more buttons 170A and 170B that may be actuated to engage and/or actuate a brake and/or a braking system that may stop movement belt 114. As shown, hand rail 112 may include a gamepad 172. In one or more embodiments, gamepad 172 may be utilized to receive user input from user 102 and/or may be utilized by user 102 to control one or more aspects of a VR environment, a VR game, and/or a VR tour, among others.

Figure 1H:
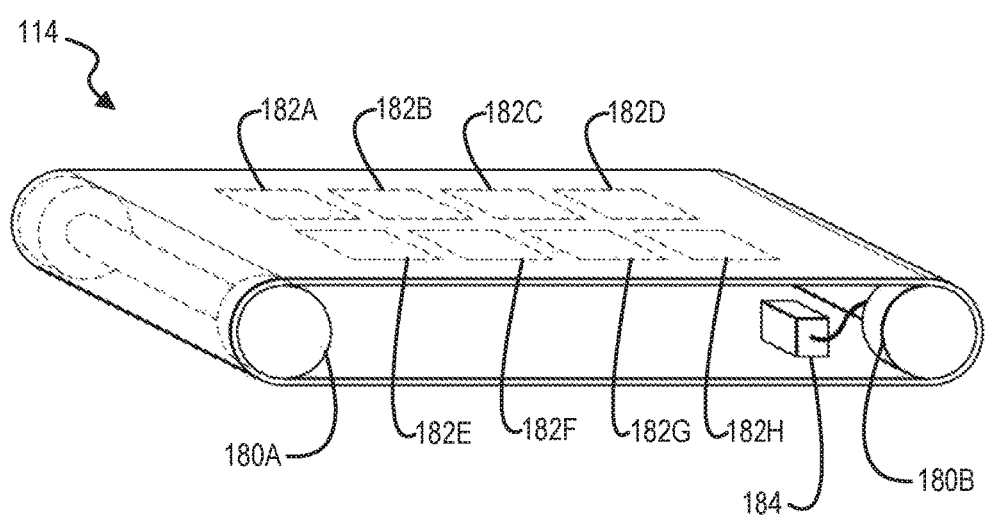
FIG. 1H illustrates further details of a movement belt, according to one or more embodiments.

As illustrated in FIG. 1H, movement belt 114 may be or include a system that includes one or more devices and/or one or more apparatuses, according to one or more embodiments. For example, movement belt 114 may include and/or move on roller shafts or axles 180. As shown, pressure sensors 182 may be included in movement belt 114 or may be located below a top portion of movement belt 114. In one or more embodiments, pressure sensors 182 may be arranged via an array, such as a grid. In one or more embodiments, pressure sensors 182 may detect and/or determine pressure applied to various points and/or positions of movement belt 114. For example, pressure sensors 182 may include electromechanical pressure sensors, which may be configured to provide pressure data and/or pressure signals to a processor. For instance, pressure sensors 182 may include force sensitive resistors and/or pressure sensitive conductors. As illustrated, a movement sensing device 184 may be coupled to roller shaft or axle 180B. In one or more embodiments, movement sensing device 184 may sense and/or determine forwards and/or backwards movements of user 102, when user 102 utilizes movement belt 114.

Figure 2:
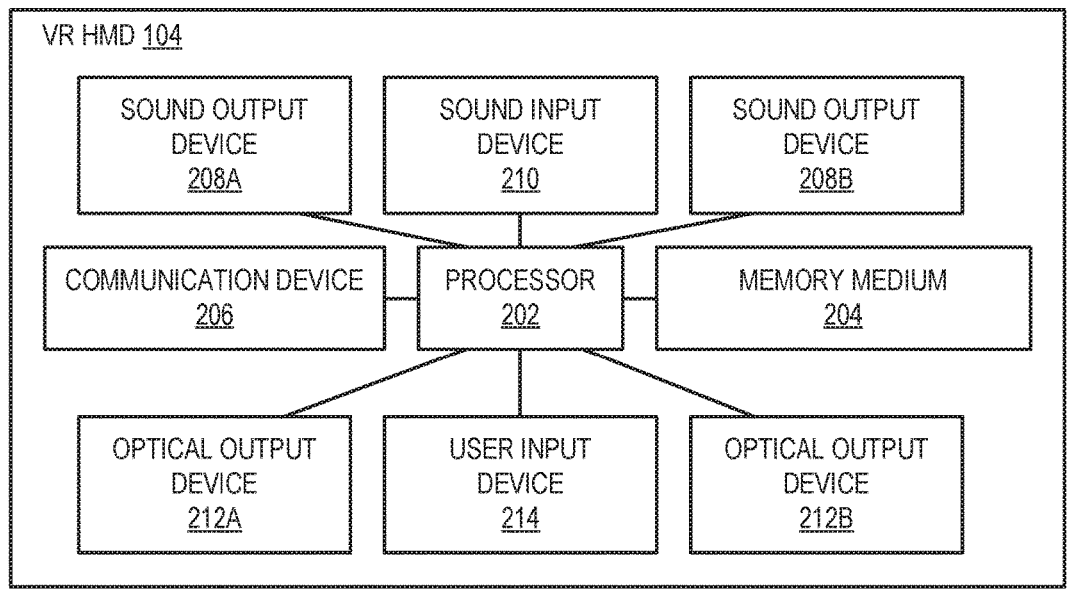
FIG. 2 illustrates further details of a virtual reality head mounted display and a virtual reality movement system, according to one or more embodiments.
Figure 2:
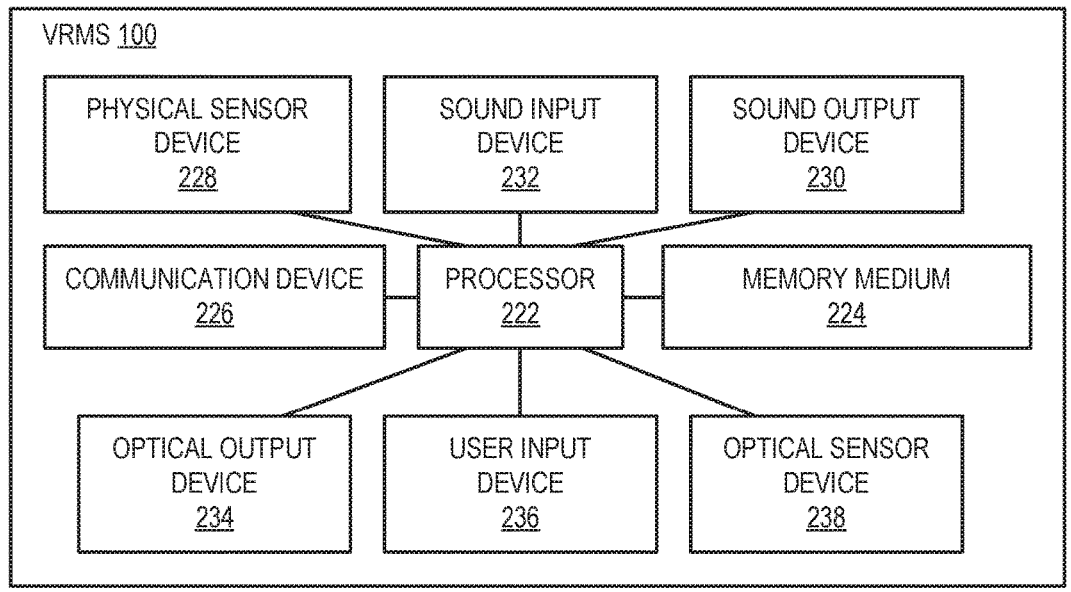

Turning now to FIG. 2, further details of a virtual reality head mounted display and a virtual reality movement system are illustrated, according to one or more embodiments. FIG. 2 provides schematic illustrations, which are not drawn to scale. As shown, VR HMD 104 may include a processor 202. In one example, processor 202 may include a microprocessor, a system-on-chip (SoC), or in general, any type of circuit that includes processing logic that executes instructions from a memory medium in implementing one or more systems, methods, and/or processes described herein. In another example, processor 202 may include a field programmable gate array (FPGA) and/or an application specific integrated circuit (ASIC), which may be configured to implement one or more systems, methods, and/or processes described herein. As illustrated, VR HMD 104 may include a memory medium 204, a communication device 206, sound output devices 208, a sound input device 210, optical output devices 212, and a user input device 214, which may be communicatively coupled to processor 202. In one or more embodiments, memory medium 204 may include data and/ or instructions, executable by processor 202, to implement one or more method, processes, and/or systems described herein. For example, memory medium 204 may include one or more volatile memory media and/or one or more non-volatile memory media.

In one or more embodiments, communication device 206 may be configured to communicate with another system. For example, communication device 206 may be configured to communicate data with VRMS 100. In one instance, communication device 206 may be configured to communicate data with VRMS 100 in a wired fashion and/or a wireless fashion. In another instance, communication device 206 may enable and/or permit VR HMD 104 to be wirelessly coupled to VRMS 100 and/or one or more portions of VRMS 100. In one or more embodiments, communication device 206 may be configured to communicate, in a wireless fashion, with one or more other systems and/or one or more other devices utilizing a radio frequency (RF) carrier and/or an optical carrier. In one example, communication device 206 may be configured to communicate, in a wireless fashion, with one or more other systems and/or one or more other devices utilizing a licensed and/or an unlicensed RF spectrum. For instance, the unlicensed spectrum may include one or more industrial, scientific, and medical (ISM) RF bands. In a second example, communication device 206 may be configured to communicate, in a wireless fashion, with one or more other systems and/or one or more other devices utilizing wireless Ethernet (e.g., based on IEEE 802.11), Bluetooth (e.g., based on IEEE 802.15), IEEE 802.15.4, and/or ZigBEE, among others. In another example, communication device 206 may be configured to communicate, in a wireless fashion, with one or more other systems and/or one or more other devices utilizing infrared (IR) signaling. In one or more embodiments, communications device 206 may include multiple communications devices configured to communicate with multiple systems and/or multiple networks. In one example, the multiple systems may be or include multiple different systems. In another example, the multiple networks may be or include multiple different networks.

In one or more embodiments, sound output devices 208 may be configured to produce one or more sounds that user 102 may hear. For example, sound output devices 208 may include one or more speakers. In one or more embodiments, sound input device 210 may be configured to receive one or more sounds. For example, sound input device 210 may include a microphone that may transform one or more sounds into one or more electrical signals (e.g., voltage signals, current signals, etc.). In one or more embodiments, optical output devices 212 may be configured produce images and/or videos. For example, optical output devices 212 may include one or more displays that may produce images and/or videos viewable by user 102.

In one or more embodiments, user input device 214 may be configured to receive input from user 102. In one example, user input device 214 may include one or more buttons and/or switches that may be actuated by user 102. In a second example, user input device 214 may include one or more dials that may be utilized by user 102. In another example, input device 214 may include one or more capacitive sensing devices. In one instance, the one or more capacitive sensing devices may include one or more capacitive sensing buttons. In another instance, the one or more capacitive sensing devices may include one or more sliders (e.g., an area that may detect sliding of a finger of user 102, etc.).

As shown, VRMS 100 may include a processor 222. In one example, processor 222 may include a microprocessor, a SoC, or in general, any type of circuit that includes processing logic that executes instructions from a memory medium in implementing one or more systems, methods, and/or processes described herein. In another example, processor 222 may include a FPGA and/or an ASIC, which may be configured to implement one or more systems, methods, and/or processes described herein. As illustrated, VRMS 100 may include a memory medium 224, a communication device 226, a sound output device 230, a sound input device 232, an optical output device 234, a user input device 236, and an optical sensor device 238, which may be communicatively coupled to processor 222. In one or more embodiments, memory medium 224 may include data and/or instructions, executable by processor 222, to implement one or more method, processes, and/or systems described herein. For example, memory medium 224 may include one or more volatile memory media and/or one or more non-volatile memory media.

In one or more embodiments, communication device 226 may be configured to communicate with another system. For example, communication device 226 may be configured to communicate data with VR HMD 104. For instance, communication device 226 may be configured to communicate data with VR HMD 104 in a wired fashion and/or a wireless fashion. In one or more embodiments, communication device 226 may be configured to communicate, in a wireless fashion, with one or more other systems and/or one or more other devices utilizing a RF carrier and/or an optical carrier. In one example, communication device 226 may be configured to communicate, in a wireless fashion, with one or more other systems and/or one or more other devices utilizing a licensed and/or an unlicensed RF spectrum. For instance, the unlicensed spectrum may include one or more ISM RF bands. In a second example, communication device 226 may be configured to communicate, in a wireless fashion, with one or more other systems and/or one or more other devices utilizing wireless Ethernet (e.g., based on IEEE 802.11), Bluetooth (e.g., based on IEEE 802.15), IEEE 802.15.4, and/or ZigBEE, among others. In another example, communication device 206 may be configured to communicate, in a wireless fashion, with one or more other systems and/or one or more other devices utilizing IR signaling. In one or more embodiments, communication device 226 may be configured to communicate with one or more devices and/or computer systems via a network. For example, the network may include and/or be coupled to a local area network (LAN), a wide area network (WAN), an Internet, a public switched telephone network (PSTN), a cellular telephone network, a satellite telephone network, or a combination of the foregoing, among others. For instance, the WAN may be or include a private WAN, a corporate WAN, and/or a public WAN, among others. In one or more embodiments, communications device 226 may include multiple communications devices configured to communicate with multiple systems and/or multiple networks. In one example, the multiple systems may be or include multiple different systems. In another example, the multiple networks may be or include multiple different networks.

In one or more embodiments, physical sensor device 228 may include one or more of a pressure sensor, a torque sensor, a micro-electro-mechanical systems (MEMS) sensor, an accelerometer, a magnetometer, and a gyroscope, among others. For example, physical sensor device 228 may sense and/or determine one or more interactions of user 102 with VRMS 100. In one instance, pressure sensors 182 may be or include physical sensor device 228, which may provide pressure data to processor 222. In another instance, movement sensing device 184 may be or include physical sensor device 228, which may provide movement data to processor 222. In one or more embodiments, sound output devices 230 may be configured to produce one or more sounds that user 102 may hear. For example, sound output devices 230 may include one or more speakers. In one or more embodiments, sound input device 232 may be configured to receive one or more sounds. For example, sound input device 232 may include a microphone that may transform one or more sounds into one or more electrical signals (e.g., voltage signals, current signals, etc.).

In one or more embodiments, optical output device 234 may be configured produce images and/or videos. For example, optical output devices 234 may include one or more displays that may produce images and/or videos viewable by user 102. In one or more embodiments, optical output device 234 may be configured to convey information to user 102 in an optical fashion. For example, optical output device 234 may include one or more light emitting diodes (LEDs) that may convey information to user 102 in an optical fashion. For instance, the one or more LEDs may convey information such as a functionality of VRMS 100, an error with VRMS 100, etc.

In one or more embodiments, user input device 236 may be configured to receive input from user 102. In one example, user input device 236 may include one or more buttons and/or switches that may be actuated by user 102. In a second example, user input device 236 may include one or more dials that may be utilized by user 102. In a third example, input device 236 may include one or more capacitive sensing devices. In one instance, the one or more capacitive sensing devices may include one or more capacitive sensing buttons. In another instance, the one or more capacitive sensing devices may include one or more sliders (e.g., an area that may detect sliding of a finger of user 102, etc.). In another example, user input device 236 may include a game pad. In one or more embodiments, optical sensor device 238 may be configured to determine movements associated with user 102. For example, optical sensor device 238 may include one or more of sensors 116 and 118, among others.

Figure 3A:
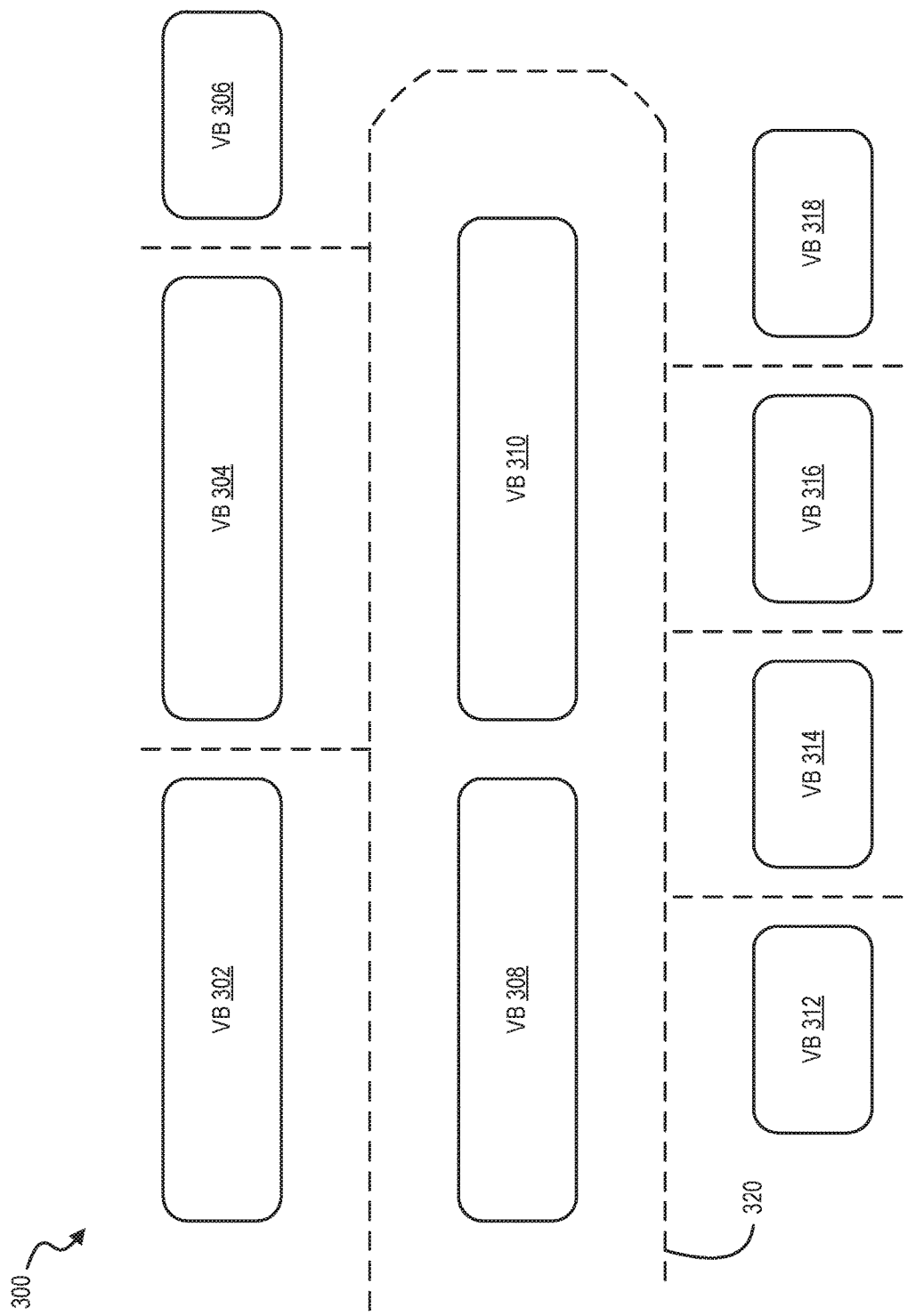
FIGS. 3A and 3B illustrate an example of a virtual reality environment, according to one or more embodiments.
Figure 3B:
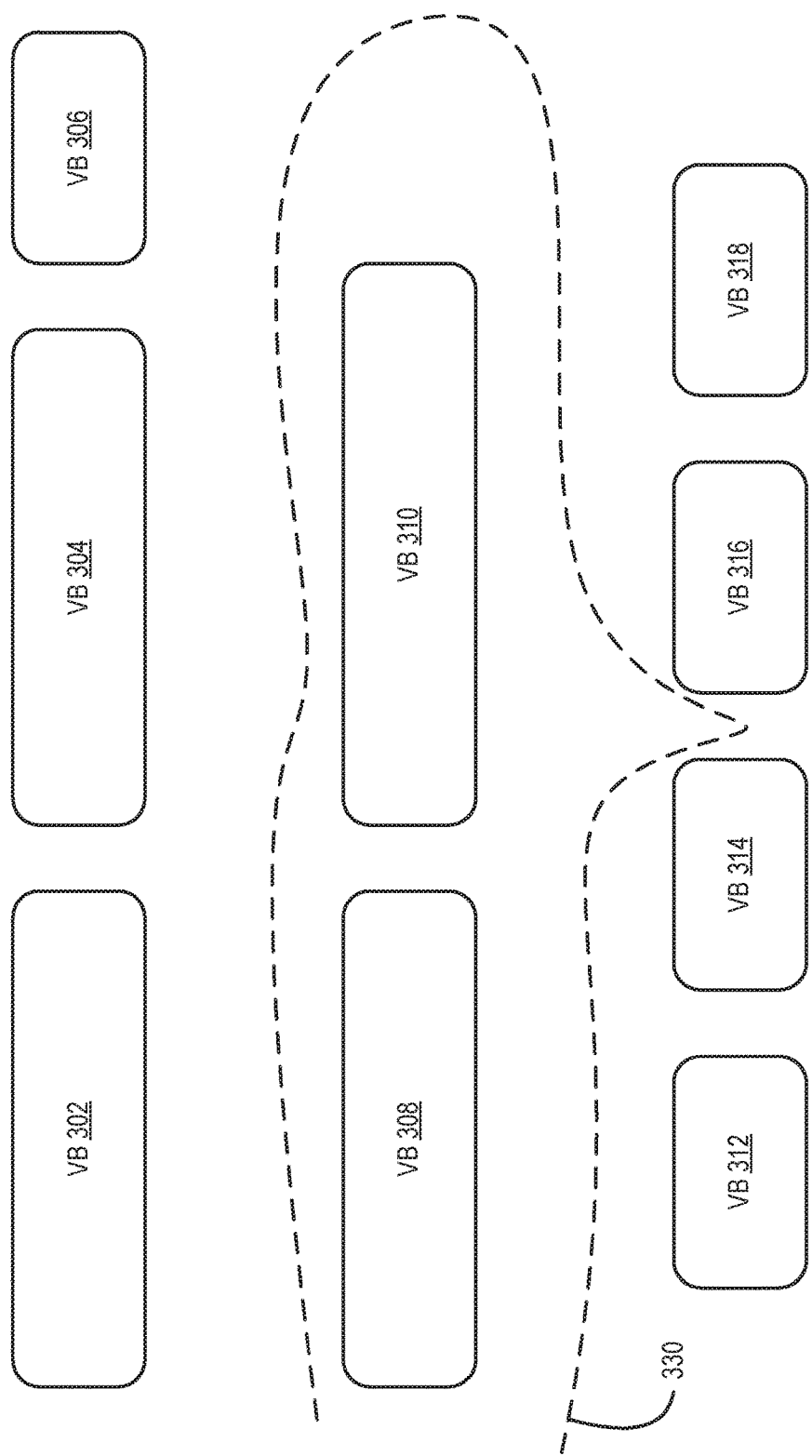

Turning now to FIGS. 3A and 3B, an example of a virtual reality environment is illustrated, according to one or more embodiments. FIGS. 3A and 3B are schematic illustrations and are not drawn to scale. As shown in FIG. 3A, a VR environment 300 may include multiple virtual buildings (VBs) 302-318. In one or more embodiments, VBs 302-318 may be or include any type of virtual structures. For example, VBs 302-318 may be or include two or more heterogeneous virtual structures. As illustrated, VR environment 300 may include a path 320. For example, user 102 may traverse, utilizing VRMS 100, path 320 and/or may traverse, utilizing VRMS 100, one or more areas and/or paths proximate to path 320. In one or more embodiments, user 102 may traverse, utilizing VRMS 100, a path 330 as illustrated in FIG. 3B. In one example, user 102 may walk, utilizing VRMS 100, path 330. In another example, user 102 may jog or run, utilizing VRMS 100, path 330.

In one or more embodiments, user 102 may have multiple dimensions of freedom when using VRMS 100 and VR environment 300. In one example, the multiple dimensions of freedom may include movement forwards, movement backwards, movement leftwards, and/or movement rightwards, among others. In another example, the multiple dimensions of freedom may include jumping, jogging, and/or running, among others. In one or more embodiments, user 102 may utilize a virtual tool (e.g., a gamepad, glove 120, controller 124, etc.) to move and/or manipulate one or more object in three dimensions. In one or more embodiments, sensor data may be applied in VRMS 100. For example, a sensor (e.g., device 126, chest belt 128, etc.) may monitor and/or determine a heart rate of user 102, and VRMS 100 VR HMD 104 may display different views of one or more images with respect to the heart rate of user 102. In one or more embodiments, user 102 may have a three hundred and sixty (360) degree view, utilizing VRMS 100, along path 320 and/or proximate to path 320 utilizing the four dimensions of freedom.

Figure 4:
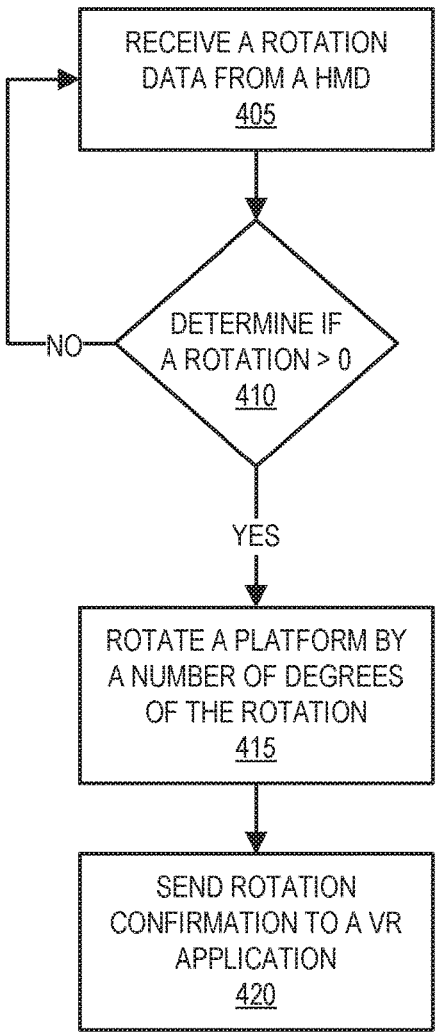
FIGS. 4-6 illustrate example methods of operating a virtual reality movement system, according to one or more embodiments.

Turning now to FIG. 4, an example of a method of operating a virtual reality movement system is illustrated, according to one or more embodiments. At 405, rotation data may be received from a HMD. For example, VRMS 100 may receive rotation data from VR HMD 104. At 410, it may be determined if a rotation is greater than zero (0) degrees. For example, VRMS 100 may determine if a rotation is greater than zero (0) degrees. For instance, VRMS 100 may determine if the rotation data indicates that a rotation is greater than zero (0) degrees.

If the rotation is not greater than zero (0) degrees, the method may proceed to 405. If the rotation is greater than zero (0) degrees, a platform may be rotated by a number of degrees of rotation, at 415. For example, VRMS 100 may rotate platform 106 by a number of degrees of rotation indicated by the rotation data. In one or more embodiments, the rotation data may indicate a direction of rotation. In one example, a positive number of degrees may indicate a rightward rotation by the number of degrees. In a second example, a negative number of degrees may indicate a leftward rotation by the number of degrees. In another example, the rotation data may include one or more numbers and/or characters that indicate leftward rotation or rightward rotation. In one instance, the rotation data may include "left" or "right". In another instance, the rotation data may include "L" or "R". In one or more embodiments, VRMS 100 may rotate platform 106 leftward or rightward, in accordance with a direction of rotation indicated by the rotation data.

At 420, a rotation confirmation may be sent to a VR application. For example, the VR application may provide a VR environment for user 102. For instance, VRMS 100 may send the rotation confirmation the VR application. In one or more embodiments, the VR application may be executed via a computer system. In one example, the computer system may be included in a cloud environment. In another example, VRMS 100 may include the computer system. In one or more embodiments, the VR application may include a game and/or a simulation.

Figure 5:
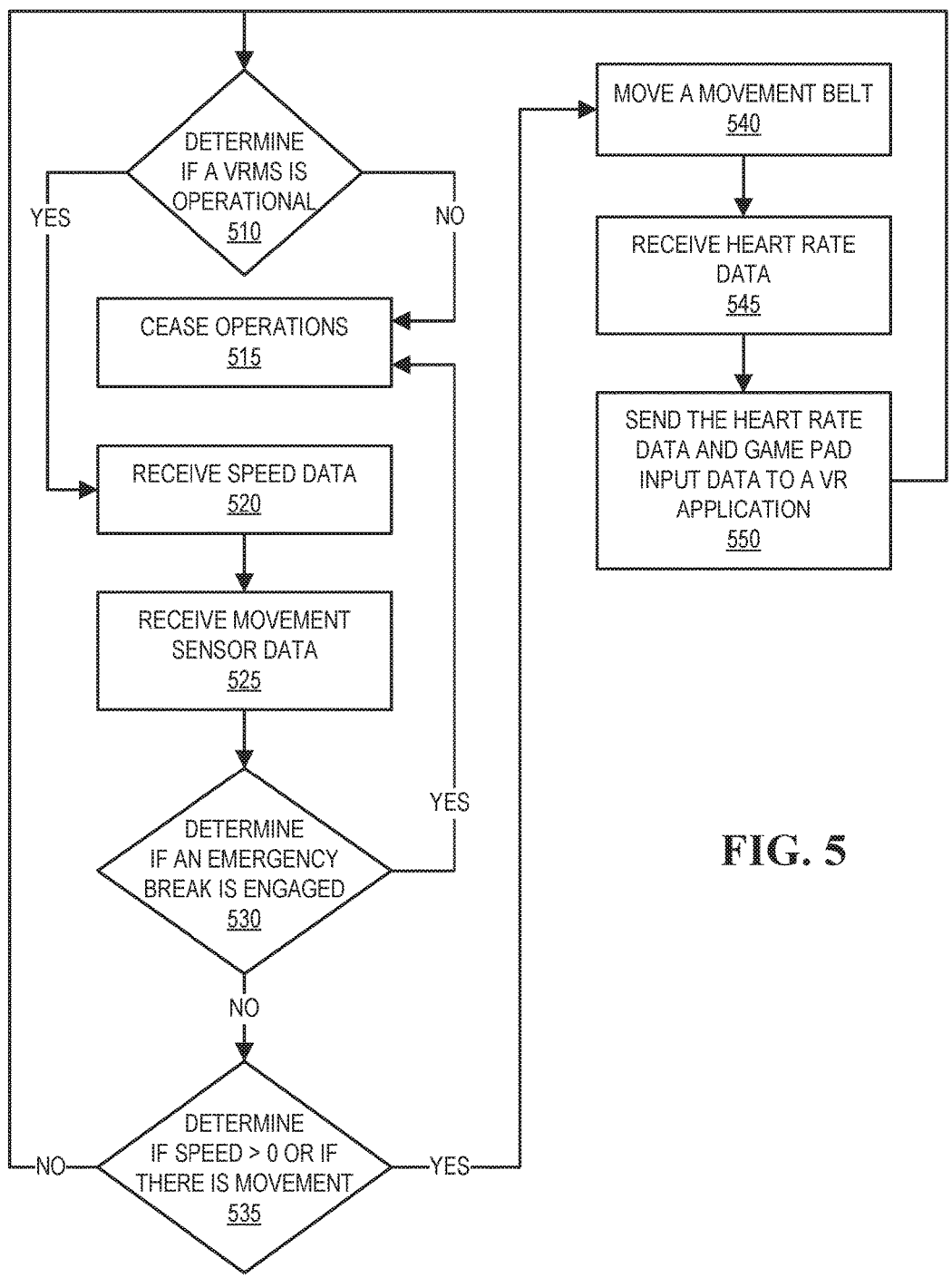

Turning now to FIG. 5, another example of a method of operating a virtual reality movement system is illustrated, according to one or more embodiments. At 510, it may be determined if a VRMS is operational. In one example, VRMS 100 may include a computer system, and the computer system of VRMS 100 may determine if VRMS 100 is operational. In another example, a VR application may determine if VRMS 100 is operational. In one instance, the VR application may be executed by another computer system. In another instance, the VR application may be a cloud-based application. In one or more embodiments, the VR application may include a game and/or a simulation.

If the VRMS is not operational, operations may cease at 515. If the VRMS is operational, speed data may be received at 520. For example, speed data may be associated with a speed of movement belt 114. At 525, movement sensor data may be received. In one example, a movement sensor may be coupled to movement belt 114. For instance, the movement sensor data may be associated with movement of movement belt 114. In a second example, the movement sensor data may be received from one or more of sensors 116 and 118. For instance, the movement sensor data may be associated with movement of one or more of legs of user 102 and/or one or more of feet of user 102. In another example, the movement sensor data may be associated with movement of a head of user 102. For instance, the movement sensor data may include rotation data.

At 530, it may be determined if an emergency brake is engaged. For example, user 102 may engage the emergency brake. For instance, one or more of rails 112 may include a button and/or switch that may be actuated that engages the emergency brake. If the emergency brake is engaged, operations may cease at 515. If the emergency brake is not engaged, it may be determined if a speed is greater than zero (0) or if there is movement, at 535. In one example, the speed may be or include a distance per time period measurement. In another example, the speed may be or include an angular measurement per time period measurement. For instance, movement belt 114 may include one or more devices that may rotate, and the speed may be an angular measurement per time period measurement of at least one of the one or more devices of movement belt 114 that may rotate.

If the speed is not greater then zero (0) and if there is no movement, the method may proceed to 510. If the speed is greater then zero (0) or if there is movement, a movement belt may be moved, at 540. For example, movement belt 114 may be moved. For instance, movement belt 114 may be moved in accordance with the speed. At 545, heart rate data may be received. For example, the heart rate data may be associated with a heart rate of user 102. In one or more embodiments, user 102 may wear a device that measures a heart rate of user 102. For example, the device that measures the heart rate of user 102 may provide the heart rate data to VRMS 100. For instance, VRMS 100 may wirelessly receive the heart rate data from the device that measures the heart rate of user 102.

At 550, the heart rate data and game pad input data may be sent to a VR application. In one or more embodiments, the VR application may be executed via a computer system. In one example, the computer system may be included in a cloud environment. In another example, VRMS 100 may include the computer system. In one or more embodiments, the method may proceed to 510.

Figure 6:
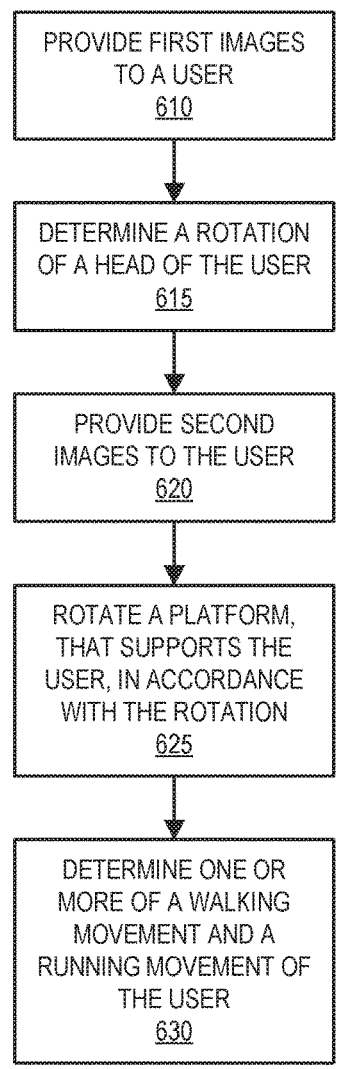

Turning now to FIG. 6, another example of a method of operating a virtual reality movement system is illustrated, according to one or more embodiments. At 610, first images may be provided to a user. For example, the first images may be or include images of a VR environment in a direction that user 102 is facing. For instance, VR HMD 104 may provide the first images to user 102.

At 615, a rotation of a head of the user may be determined. For example, a rotation of a head of user 102 may be determined. For instance, VR HMD 104 may determine the rotation of the head of user 102. In one or more embodiments, VR HMD 104 may include sensors that may determine the rotation of the head of user 102. For example, the sensors may include one or more of a gyroscope and an accelerometer. In one or more embodiments, VRMS 100 may determine the rotation of the head of user 102. For example, VRMS 100 may receive data from one or more sensors (e.g., a gyroscope, an accelerometer, etc.) of VR HMD 104 and determine the rotation of the head of user 102 based at least on the data from the one or more sensors of VR HMD 104.

At 620, second images may be provided to the user. For example, the second images may be or include images of the VR environment in a direction that user 102 has rotated. For instance, VR HMD 104 may provide the second images to user 102. At 625, a platform that supports the user may be rotated in accordance with the rotation. For example, VRMS 100 may rotate platform 106 in accordance with the rotation. For instance, platform 106 may be rotated on platform 108. In one embodiment, rotating platform 106 in accordance with the rotation may include a one-to-one correspondence. For example, if the rotation is forty-seven (47) degrees, platform 106 may be rotated forty-seven (47) degrees. In one or more embodiments, rotating platform 106 in accordance with the rotation may include a ratio. For example, if the rotation is a number of degrees, platform 106 may be rotated by the number of degrees modified by the ratio.

At 630, one or more of a walking movement and a running movement of the user may be determined. For example, VRMS 100 may determine one or more of a walking movement and a running movement of user 102 via one or more sensors. In one instance, the sensors may include one or more of sensors 116 and 118. In another instance, the sensors may include one or more of sensors may include one or more sensors coupled to movement belt 114 (e.g., a torque sensor, a pressure sensor, etc.). At 635, a movement belt may be moved in accordance with the one or more of the walking movement and the running movement of the user. For example, VRMS 100 may move movement belt 114 in accordance with the one or more of the walking movement and the running movement of user 102.

In one or more embodiments, one or more of the method elements described herein and/or one or more portions of an implementation of any method element may be repeated, may be performed in varying orders, may be performed concurrently with one or more of the other method elements and/or one or more portions of an implementation of any method element, or may be omitted. Further, one or more of the system elements described herein may be omitted and/or additional system elements may be added as desired, according to one or more embodiments. Moreover, supplementary, additional, and/or duplicated method elements may be instantiated and/or performed as desired, according to one or more embodiments. The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system, comprising:
 a processor;
 a storage medium coupled to the processor and that stores instructions executable by the processor;
 a first platform that has a top surface that is substantially planar and that is configured to rotate and support a user;
 one or more handrails attached to the first platform and including a controller;
 when the processor executes the instructions, the system:
 provides first images to a user;

determines a rotation of a head of the user;
provides second images, based at least on the rotation of the head of the user, to the user; and
rotates the first platform in accordance with the rotation of the head of the user.

2. The system of claim 1, wherein
the first platform includes a movement belt that is substantially planar; and
the system further:
determines one or more of a walking movement and a running movement of the user; and
moves the movement belt in accordance with the one or more of the walking movement and the running movement of the user.

3. The system of claim 2, further comprising:
one or more optical sensors coupled to the processor and configured to determine one or more movements of the user;
wherein the system further determines the one or more of the walking movement and the running movement of the user via the one or more optical sensors.

4. The system of claim 1, wherein the system further determines the rotation of the head of the user via one or more of a gyroscope and an accelerometer.

5. The system of claim 1, further comprising:
a virtual reality head mounted display configured to be wirelessly coupled to the processor and configured to be worn by the user;
wherein the system further determines the rotation of the head of the user via the virtual reality head mounted display.

6. The system of claim 5, wherein
the head mounted display is further configured to provide the first images and the second images to the user;
the system further provides the first images to the head mounted display; and
the system further provides the second images to the head mounted display.

7. The system of claim 1, further comprising:
a second platform;
wherein the first platform is further configured to rotate on the second platform; and
wherein the system further rotates the first platform on the second platform in accordance with the rotation of the head of the user.

8. A method, comprising:
providing first images to a user;
determining a rotation of a head of the user;
providing second images, based at least on the rotation of the head of the user, to the user;
rotating a platform, that has a top surface that is substantially planar and that is configured to support the user, in accordance with the rotation of the head of the user; and
enabling the user to control the first images and the second images using a controller provided on one or more handrails attached to the platform.

9. The method of claim 8, further comprising:
determining one or more of a walking movement and a running movement of the user; and
moving a movement belt, that is substantially planar, in accordance with the one or more of the walking movement and the running movement of the user.

10. The method of claim 9, further comprises determining the one or more of the walking movement and the running movement of the user via one or more optical sensors.

11. The method of claim 8, further comprising determining the rotation of the head of the user via one or more of a gyroscope and an accelerometer.

12. The method of claim 8, further comprising determining the rotation of the head of the user via a virtual reality head mounted display configured to be worn by the user.

13. The method of claim 12, wherein
the providing the first images to the user includes the virtual reality head mounted display providing the first images to the user; and
the providing the second images based at least on the rotation includes the virtual reality head mounted display providing the second images to the user.

14. The method of claim 1, further comprises rotating the platform on another platform.

15. A computer-readable non-transitory storage medium storing instructions executable by a processor of a system to execute a process, the process comprising:
providing first images to a user;
determining a rotation of a head of the user;
providing second images, based at least on the rotation of the head of the user, to the user;
rotating a first platform, that has a top surface that is substantially planar and that is configured to support the user, in accordance with the rotation of the head of the user; and
enabling the user to control the first images and the second images using a controller provided on one or more handrails attached to the platform.

16. The computer-readable non-transitory storage medium of claim 15, wherein
the first platform includes a movement belt that is substantially planar;
the process further comprises:
determining one or more of a walking movement and a running movement of the user; and
moving the movement belt in accordance with the one or more of the walking movement and the running movement of the user.

17. The computer-readable non-transitory storage medium of claim 16, wherein the process further comprises determining the one or more of the walking movement and the running movement of the user via one or more optical sensors.

18. The computer-readable non-transitory storage medium of claim 15, wherein the process further comprises determining the rotation of the head of the user via one or more of a gyroscope and an accelerometer.

19. The computer-readable non-transitory storage medium of claim 15, wherein the process further comprises determining the rotation of the head of the user via a virtual reality head mounted display that is wirelessly coupled to the system and configured to be worn by the user.

20. The computer-readable non-transitory storage medium of claim 19, wherein:
the head mounted display is further configured to provide the first images and the second images to the user;
the process further comprises providing the first images to the head mounted display;
the process further comprises providing the second images to the head mounted display; and
the first images and the second images are images of a virtual tour.

* * * * *